United States Patent [19]

Sylvanowicz et al.

[11] Patent Number: 5,702,370
[45] Date of Patent: *Dec. 30, 1997

[54] SELF-SEALING GUIDEWIRE AND CATHETER INTRODUCER

[75] Inventors: John T. Sylvanowicz, Andover; George W. Bourne, IV, N. Chelmsford, both of Mass.

[73] Assignee: C. R. Bard, Inc., Murray Hill, N.J.

[*] Notice: The term of this patent shall not extend beyond the expiration date of Pat. No. 5,304,156.

[21] Appl. No.: 228,666

[22] Filed: Apr. 18, 1994

Related U.S. Application Data

[63] Continuation of Ser. No. 817,941, Jan. 2, 1992, Pat. No. 5,304,156, which is a continuation of Ser. No. 674,707, Mar. 25, 1991, abandoned, which is a continuation of Ser. No. 550,454, Jul. 10, 1990, abandoned, which is a continuation of Ser. No. 397,761, Aug. 23, 1989, abandoned, which is a continuation of Ser. No. 201,538, Jun. 2, 1988, abandoned.

[51] Int. Cl.$^6$ .................................................. A61M 5/00
[52] U.S. Cl. ........................................ 604/256; 251/149.1
[58] Field of Search ................................ 604/167, 169, 604/280, 247, 283, 256; 137/849; 251/149.1

[56] References Cited

U.S. PATENT DOCUMENTS

| | | | |
|---|---|---|---|
| 4,000,739 | 1/1977 | Stevens | 604/167 |
| 4,424,833 | 1/1984 | Spector et al. | 604/167 |
| 4,430,081 | 2/1984 | Timmermans | 604/167 |
| 4,475,548 | 10/1984 | Muto | 604/167 |
| 4,610,665 | 9/1986 | Matsumoto et al. | 604/256 |
| 4,610,674 | 9/1986 | Suzuki et al. | |
| 4,649,904 | 3/1987 | Krauter et al. | |
| 4,655,752 | 4/1987 | Honkanen et al. | 604/256 |
| 4,705,511 | 11/1987 | Kocak | 604/167 |
| 4,798,594 | 1/1989 | Hillstead | |
| 4,809,679 | 3/1989 | Shimonaka et al. | 604/167 |
| 4,857,062 | 8/1989 | Russell | |
| 4,886,507 | 12/1989 | Patton et al. | |
| 4,895,565 | 1/1990 | Hillstead | 604/256 |
| 4,929,235 | 5/1990 | Merry et al. | |
| 4,932,633 | 6/1990 | Johnson et al. | |
| 4,960,412 | 10/1990 | Fink | |
| 5,000,745 | 3/1991 | Guest et al. | |
| 5,009,391 | 4/1991 | Shegerwald | |
| 5,059,186 | 10/1991 | Yomamoto et al. | |
| 5,084,023 | 1/1992 | Lemieux | |
| 5,098,393 | 3/1992 | Amplatz et al. | |
| 5,104,389 | 4/1992 | Deem et al. | |
| 5,114,408 | 5/1992 | Fleischhaker | |
| 5,125,910 | 6/1992 | Freitas | |
| 5,167,637 | 12/1992 | Okada et al. | |
| 5,195,980 | 3/1993 | Catlin | |
| 5,211,634 | 5/1993 | Vallancourt | |
| 5,242,413 | 9/1993 | Heiliger | |
| 5,242,428 | 9/1993 | Palestront | |
| 5,254,097 | 10/1993 | Schock et al. | |
| 5,267,982 | 12/1993 | Sylvanowicz | |
| 5,273,545 | 12/1993 | Hunt | |
| 5,304,156 | 4/1994 | Sylvanowicz et al. | 604/256 |

FOREIGN PATENT DOCUMENTS

| | | |
|---|---|---|
| 143518 | 6/1985 | European Pat. Off. |
| 344907 | 12/1989 | European Pat. Off. |
| 442194 | 8/1991 | European Pat. Off. |
| WO93/25252 | 12/1993 | WIPO |

*Primary Examiner*—Mark Bockelman
*Attorney, Agent, or Firm*—Arthur Z. Bookstein

[57] ABSTRACT

A self-sealing catheter and guidewire introducer has a self-sealing gasket adapted to effect a seal when a catheter or guidewire extends through the gasket as well as when neither extends through the gasket.

22 Claims, 2 Drawing Sheets

SELF-SEALING GUIDEWIRE AND CATHETER INTRODUCER

This application is a continuation of application Ser. No. 07/817,941, filed Jan. 2, 1992, now U.S. Pat. No. 5,304,156, which is a continuation of application Ser. No. 07/674,707, filed Mar. 25, 1991, now abandoned, which is a continuation of application Ser. No. 07/550,454, filed Jul. 10, 1990, now abandoned, which is a continuation of application Ser. No. 07/397,761, filed Aug. 23, 1989, now abandoned, which is a continuation of application Ser. No. 07/201,538, filed Jun. 2. 1988, now abandoned.

FIELD OF THE INVENTION

This invention relates to improvements in hemostasis catheter introducers used in the insertion and removal of catheters and guidewires from a patient's blood vessel. More particularly, the invention relates to an introducer having a self-sealing gasket which prevents back bleeding with inserted devices such as relatively slender guidewires as well as more substantial diameter catheters.

BACKGROUND OF THE INVENTION

U.S. Pat. No. 4,424,833 (Spector et al.) discloses a catheter introducer having a self-sealing gasket adapted to maintain a seal and prevent back bleeding both when the catheter is in place through the introducer as well as when the catheter is removed. The Spector et al. device also includes a side entry port through which liquids may be introduced or through which the device may be aspirated. The device is effective to provide a self-sealing gasket that maintains its seal over a relatively wide range of pressures to include not only the normal positive pressure of the patient's blood but also the reduced pressure which results from aspirations through the side port. The device also displays the desirable feature that its self-sealing function is achieved without unduly inhibiting axial and rotary movement of the catheter as it passes through the seal.

Although the foregoing device maintains an effective seal with a catheter passing through it as well as when the catheter is not present, it is somewhat limited in the range of diameters of devices that can be passed through it while maintaining a seal. In particular, guidewires, which typically are used in association with catheters, are of significantly smaller diameter than the catheters and when passed through the gasket, do not maintain an effective seal with the gasket. The guidewires, however, are sufficiently large to break the seal which permits blood to leak out of the proximal end of the device. Therefore, it would be desirable to provide a device having a self-sealing structure that is effective to provide a seal when a catheter as well as when a guidewire extends through the introducer. Moreover, such a device also should be effective to maintain the seal when neither the guidewire nor catheter are in place as well as during aspiration and over a relatively wide range of pressures. Further, such a device should not unduly inhibit axial as well as rotary movement of the catheter or the guidewire. It is among the general objects of the invention to provide such an improved gasketed introducer.

SUMMARY OF THE INVENTION

The self-sealing gasket is molded in a single piece from a resilient material, preferably from a high durometer elastomer to have a predetermined thickness. The outer half thickness of the gasket has a central hole, slightly smaller in diameter than the diameter of the guidewire that will be received in the device, and which will form a seal about the guidewire. The inner half thickness of the gasket is provided with a plurality of radially extending slits which extend to a depth slightly greater than to the middle of the thickness of the gasket. The combination of the slits and the central hole define an arrangement which is effective to make a seal against a guidewire as well as with a much larger diameter catheter and without unduly inhibiting movement of either of the guidewire or catheter through the gasket. The arrangement defines a number of flaps which normally close the central aperture in the absence of a guidewire or a catheter. When a guidewire is inserted into the device, the flaps spread apart and a seal is made against the guidewire by the periphery of the central hole in the outer face of the gasket. When a larger diameter catheter is inserted through the device, the resilience of the gasket enables the hole to enlarge. Restriction on the movement of the catheter, however, is minimized because the inner thickness of the gasket, being slit, it readily yields and presents no significant constricting force about the catheter. The constricting, sealing force about the catheter is provided only by the unslit thickness of the gasket.

It is among the general objects of the invention to provide an improved self-sealing gasket in a catheter introducer.

A further object of the invention is to provide a catheter introducer having a self-sealing gasket adapted to effect a seal with a guidewire as well as with a catheter but without unduly restricting the ability of the guidewire or catheter to be manipulated therethrough.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENT

Figure 1:
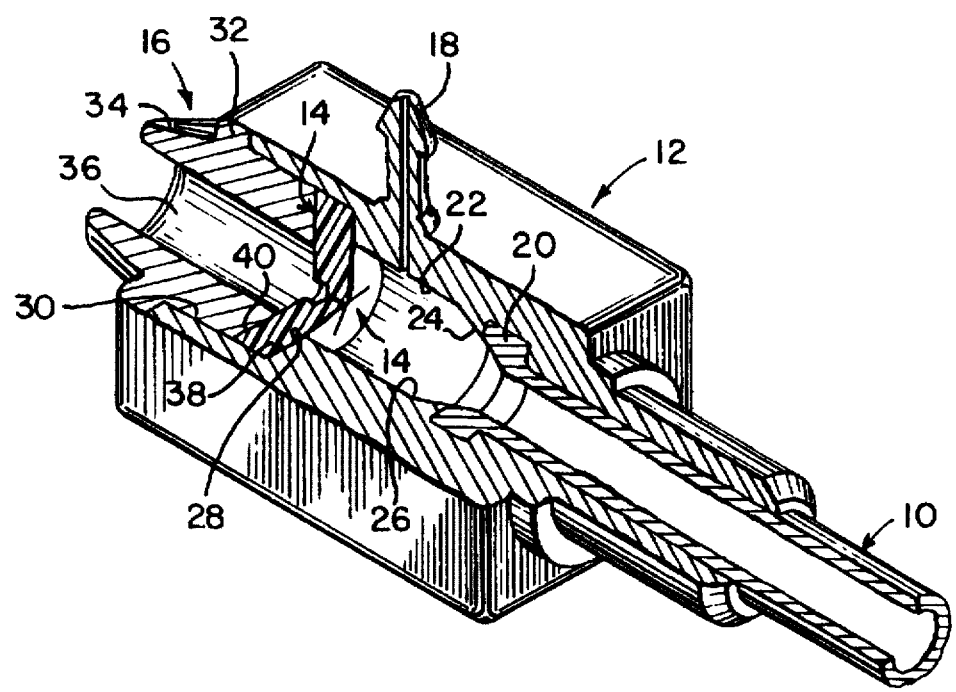
FIG. 1 is an illustration of the invention as embodied in the housing of catheter introducer broken away in section to illustrate the internal structure of the device.

FIG. 1 shows a catheter introducer incorporating the present invention. The introducer includes an introducer tube 10 which is connected to and extends from a housing 12. The one-piece molded self-sealing gasket, indicated generally by the reference character 14 is mounted in the valve housing 12 as described more fully below. The gasket 14 is retained firmly in place in the housing 12 by an end cap 16. The housing 12 preferably is provided with a side port 18.

The introducer tube 10 may be formed from a fluorinated plastic and is formed separately with an enlarged head portion 20. The housing 12 preferably is molded directly onto the headed end of the introducer tube 10 and is locked securely and integrally with the introducer tube 10 by engagement with the head portion 20. The housing 12 is formed with a hollow interior 22 which forms a forwardly tapering configuration indicated at 24, which merges smoothly with the tapering inlet and of the head portion 20 of the introducer tube 10. The side port 18 is molded integrally with the housing to provide a means to communicate directly with the hollow interior 22 of the housing 12.

The hollow interior 22 of the housing 12 defines a cylindrical bore 26 which terminates in an enlarged diameter shoulder 28. The shoulder 28 terminates in an enlarged diameter outer bore 30 which receives the end cap 16. The end cap 16 has an inner portion dimensioned to fit snugly within the outer bore 30. The cap 16 includes an outer peripheral collar 32 which engages the outer end of the housing to determine and limit precisely the extent to which the inner end of the cap 16 extends into the outer bore 30. The outer end of the end cap 16 may include an extension 34 and a tapered inlet opening 36 may be formed through the end cap. The inlet 36 is tapered to enable a conventional luer connector to be attached, if desired.

As shown in FIG. 1, the self-sealing gasket 14 is retained between the end cap 16 and the shoulder 28 of the housing. The shoulder 28 preferably is provided with a circular ridge 38 and an identical ridge 40 is formed on the facing inner surface of the inner end of the end cap 16. When the end cap 16 is fully seated, as determined by engagement of the collar 32 with the end of the housing 12, the ridges 38, 40 engage and effect a firm grip on the gasket 14.

Figure 2:
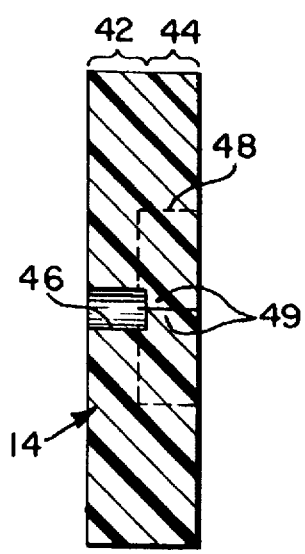
FIG. 2 is an enlarged sectional illustration of the one-piece self-sealing valve element of the present invention.
Figure 3:
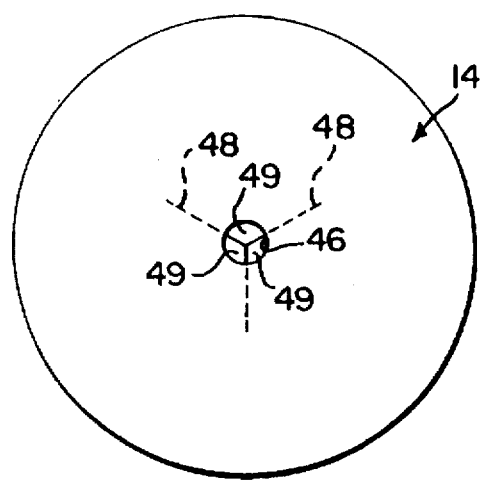
FIG. 3 is an illustration of the self-sealing valve member as viewed from the left (proximal) face of FIG. 2.

As shown in enlarged detail in FIGS. 2–5, the gasket 14 may be considered as having an inwardly facing surface, an outwardly facing surface, an outer half thickness 42 and an inner half thickness 44. The outer half thickness 42 is formed with a central aperture 46 which extends only to a depth of about the half thickness of the gasket 14. As shown in FIGS. 2 and 3, the central aperture 46 may be considered as defined by a circumferential wall and a bottom wall. The inner half thickness of the gasket is formed with a plurality (preferably three) of radially extending slits 48 which extend slightly greater than to the half thickness of the gasket 14 so that the slits extend into the surrounding circumferential wall defining the central aperture. In other words, the sum of the depth of the slits and the aperture is greater than the thickness of the gasket. The slits 48 overlap the central aperture 46 to define three approximately triangularly shaped flaps 49 that overlap the central aperture 46. The diameter of the central aperture 46 is selected so that it will effect a seal with the guidewires with which the device may be used. The radially extending slits 48, on the inner face of the gasket 14 should extend radially a distance that is slightly greater than the maximum diameter of catheter with which the device is to be used. By way of example, for a maximum catheter diameter of the order of 0.104" (8 French) the disk-shaped gasket may be 0.310" in diameter and 0.070" thick. The central aperture 46 may be approximately 0.029" diameter, that diameter being adapted to effect a seal with conventional size guidewires of the order of 0.035" to about 0.038". The central aperture depth is about 0.035".

The length of the radial slits is important in that if the slits 48 are too long, the flaps 49 will tend to fold in a manner that increases the drag of the guidewire and/or catheter but if the slits are too short, the resulting flaps are too stiff and will unduly restrict movement of the guidewire and catheter. We have found that for a gasket as described above a radial length of about 0.075 for the slits 48 is ideal to accept catheters of 5 French to 3 French size.

From the foregoing, it will be appreciated that the inner portions of the slits define a central region that overlaps the central aperture and that the more radially outwardly disposed portions of the slits extend into a region disposed radially outwardly of the region of the aperture.

It is very desirable that the gasket 14 be molded from a comparatively hard, low friction resilient material, such as a high durometer silicone rubber having a hardness of at least 35 A and preferably between 35 A and 60 A and most preferably near 50 A on the Shore A Scale. The gasket preferably is lubricated with a silicone oil.

Figure 4:
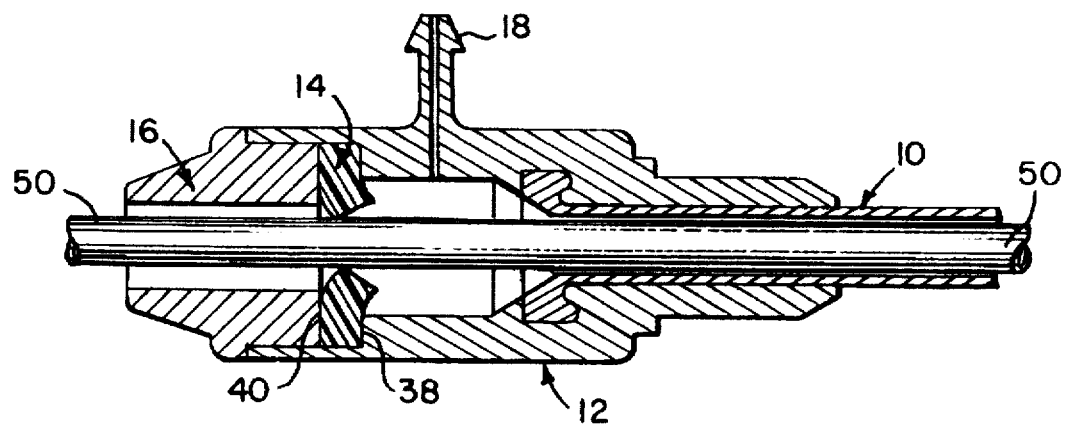
FIG. 4 is an illustration of the device having a catheter extending through the introducer with the gasket deformed to receive the catheter in self-sealing configuration.

FIG. 4 illustrates the configuration of the gasket 14 with a catheter 50 extending therethrough. As can be seen, the catheter 50 forces enlargement of the central aperture 46 in the outer half thickness 42 of the gasket 14, and it is that portion of the gasket that provides the constricting and sealing force. That force is not too great to adversely impair catheter movement because it is affected only by half of the thickness of the gasket, the inner half thickness of the gasket 44 in the region radially outwardly of the central aperture 46 being slit and providing no substantial constricting force.

Figure 5:
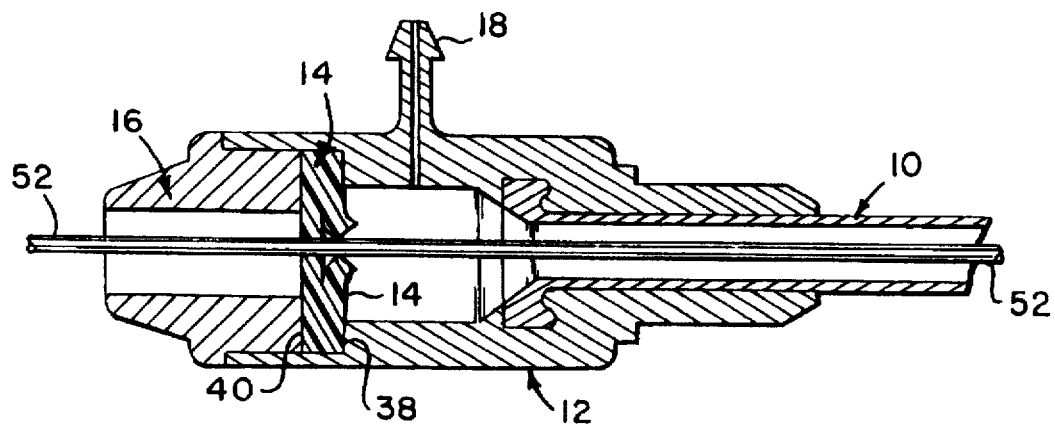
FIG. 5 is an illustration of the device similar to FIG. 4 with a guidewire extending therethrough.

FIG. 5 illustrates the manner in which the gasket 14 effects a seal about a guidewire 52. The seal is effected by the periphery of the central aperture 46 which is slightly smaller in diameter than the diameter of the guidewire 51. The flaps 49 formed through the inner half thickness 44 of the gasket 14 and are defined by the portion of the radial slits 48 that overlap and intersect the central aperture 46, separate as shown, to permit free movement of the guidewire 52. As mentioned above, the stiffness of the material, as measured by the Shore A Scale, is no less than about 35 A and preferably is of the order of 50 A. When both the catheter and the guidewire are removed, the flaps 49 close thereby providing a seal to prevent back bleeding.

In using the device, the introducer tube 10 is inserted into a patient's blood vessel, typically percutaneously. Once the introducer is in place it may be sutured to the patient's skin to secure it Thereafter, guidewires and catheters may be introduced through the self-sealing gasket 14 in housing 12 and catheter changes may be made as desired. When using angiographic procedures or other surgical techniques in which the physician must be able to feel obstructions to the advancing catheter or guidewire tip by feeling resistance at the proximal end of the catheter, the resistance offered by the valve 14 of the present invention does not significantly impair the physician's feel. The side port 18, of course, may be used in the manner in which side ports are normally used, such as to infuse medicine, intravenous nourishment or to take blood pressure measurements. The side port may be aspirated to withdraw blood samples if desired, and in aspiration, the device is quite satisfactory.

The gasket is easy to make and assemble in the introducer body.

It should be understood that the foregoing description of the invention is intended merely to be illustrative thereof and that other modifications and embodiments may be apparent to those skilled in the art without departing from its spirit.

Having thus described the invention, what I desire to claim and secure by Letters Patent is:

1. An introducer adapted to be inserted into a patient's blood vessel comprising:

a housing having an introducer sheath extending from an end of the housing, the sheath being adapted to be inserted into a patient's blood vessel, the housing having an opening at its other end;

a self-sealing, one piece gasket having a thickness and inwardly and outwardly facing surfaces, the gasket being mounted in the housing with at least part of its outwardly facing surface being exposed at the opening;

the gasket having a central aperture in its outwardly facing surface extending a predetermined depth into the gasket, the aperture being defined by a circumferential wall and bottom wall;

the inwardly facing surface of the gasket being formed with a plurality of radially extending slits, the depth of the slits being such that the slits extend into the bottom wall and the circumferential wall, the central region of the slits overlapping the central aperture, the depths of each of the aperture and the slits being less than the thickness of the gasket;

the central aperture and the slits being dimensioned to seal a wide range of diameters of devices including both guidewires and catheters extended through the aperture, the radius of the aperture being less than the radial length defined by the slits.

2. The device as defined in claim 1 wherein the gasket is formed from a molded elastomeric material having a Shore A durometer of between about 35 A and 60 A.

3. The device as defined in claim 2 wherein the Shore A durometer is 50 A.

4. The device as defined in claim 1 wherein the gasket is lubricated with a silicone oil.

5. The device as defined in claim 1 wherein the housing includes an inner bore and an outer bore, the outer bore being larger than the inner bore and defining a shoulder at the juncture of the inner bore and the outer bore, the gasket having a diameter corresponding substantially to that of the outer bore;

the gasket being secured in the housing by a cap receivable in the outer bore of the housing and being adapted to tightly compress the periphery of the gasket against the shoulder.

6. The device as defined in claim 1 wherein the guidewires and catheters range in diameter from 0.037 inch to 0.104 inch.

7. An introducer adapted for insertion into a patient's blood vessel comprising:

a housing having an introducer sheath extending from a first end of the housing, the sheath being adapted for insertion into a patient's blood vessel, the housing having an opening at a second end thereof;

a self-sealing, one-piece gasket mounted in the housing and including an outwardly facing surface being exposed through said opening, a central aperture having a circumferential wall and a bottom wall, the aperture extending a first depth into the gasket from the outwardly facing surface;

the gasket having a plurality of radially extending slits extending a second depth into the gasket from an inwardly facing surface of the gasket such that the slits extend into the circumferential wall, the depths of each of the aperture and the slits being less than the thickness of the gasket; and the slits defining a weakened annular region of the gasket about the aperture to reduce resistance against passing catheters through the aperture such that the gasket can seal a wide range of diameters of devices including both guidewires and catheters.

8. A hemostasis gasket for use in a catheter apparatus comprising:

a self-sealing one piece gasket having a thickness, an inwardly facing surface, an outwardly facing surface, and a central aperture in its outwardly facing surface, the aperture extending a predetermined depth into the gasket and being defined by a circumferential wall and a contiguous bottom wall;

a plurality of slits formed in the inwardly facing surface of the gasket and extending radially from a central region, the slits having a depth such that they intersect the circumferential wall, the central region of the slits overlapping the central aperture and defining a plurality of flaps normally closing the aperture, the depths of each of the aperture and the slits being less than the thickness of the gasket;

the central aperture and the slits being dimensioned to effect and enable the gasket to seal about a range of diameters of devices that includes guidewires and catheters.

9. The gasket of claim 8 wherein the radius of the central aperture is substantially less than the radius defined by each of the slits.

10. The gasket of claim 8 wherein the plurality of slits formed in the gasket is at least three.

11. The gasket of claim 8 wherein the sum of the aperture depth and the slit depth is greater than the thickness of the gasket.

12. The gasket of claim 8 wherein the predetermined aperture depth is substantially equal to one half the thickness of the gasket, and the slit depth is greater than one-half the thickness of the gasket.

13. The gasket of claim 8 wherein the gasket is formed from a molded elastomeric material having a Shore A durometer of between about 35 A and 60 A.

14. The gasket of claim 13 wherein the Shore A durometer is 50 A.

15. The gasket of claim 8 wherein the sum of the aperture depth and the slits depth is no less than the gasket thickness.

16. A hemostasis gasket for use in a catheter apparatus comprising:

a self-sealing, one-piece gasket having a thickness, an inwardly facing surface, an outwardly facing surface, and a central aperture in its outwardly facing surface, the aperture having a bottom wall and extending a predetermined depth into the gasket;

a plurality of slits having a predetermined depth formed in the inwardly facing surface of the gasket and extending radially from a central region;

neither of the depths of the aperture and the slits extending from the inwardly facing surface to the outwardly facing surface of the gasket;

the sum of the aperture depth and the slits depth being greater than the thickness of the gasket;

the central aperture and the slits being dimensioned to seal about a range of diameters of devices that includes guidewires and catheters.

17. A hemostasis gasket for use in a catheter apparatus comprising:

a self-sealing, one-piece gasket having a thickness, an inwardly facing surface, an outwardly facing surface and a central aperture in its outwardly facing surface, the aperture having a bottom wall and extending a predetermined depth into the gasket;

a plurality of slits having a predetermined depth formed in the inwardly facing surface of the gasket and extending radially from a central region;

neither of the depths of the aperture and the slits extending from the inwardly facing surface to the outwardly facing surface of the gasket;

the central aperture and the slits being dimensioned to seal about a range of diameters of devices that includes guidewire and catheters;

the sum of the aperture depth and the slit depth is greater than the thickness of the gasket.

18. A hemostasis gasket for use in a catheter apparatus comprising:
- a self-sealing one piece gasket having a thickness, an inwardly facing surface, an outwardly facing surface, and a central aperture in its outwardly facing surface, the aperture having a bottom wall and extending a predetermined depth into the gasket;
- a plurality of slits having a predetermined depth formed in the inwardly facing surface of the gasket, each slit extending radially from a central region; and
- the depths of each of the aperture and the slits being less than the thickness of the gasket;
- a discontinuity extending a predetermined depth into the inwardly facing surface in the region that is radially outward of the region defined by the aperture.

19. The gasket of claim 18 wherein the central aperture terminates at a bottom wall that intersects the central region of the slits.

20. A method of making a hemostasis gasket for use in a catheter apparatus, comprising:
- providing a self-sealing one piece resilient gasket having a thickness, an inwardly facing surface, and an outwardly facing surface;
- forming a central aperture having a bottom wall and a predetermined depth into the outwardly facing surface;
- radially slitting the inwardly facing surface of the gasket in the region of the aperture to a predetermined depth wherein the sum of the radial slit depth and the aperture depth is no less than the thickness of the gasket and where each of the depths of the slits and the aperture is less than the thickness of the gasket; and
- slitting the inwardly facing surface of the gasket to a predetermined depth in the region that is radially outward of the region defined by the aperture, whereby the slits in the region of the aperture define resilient flaps that normally close the aperture and the slits in the region radially outward of the aperture define a weakened region about the region defined by the aperture.

21. The method of making the gasket of claim 20 wherein the central region of the radial slits intersect a bottom wall of the aperture.

22. A method of making a hemostasis gasket for use in a catheter apparatus comprising:
- providing a self-sealing one piece resilient gasket having a thickness, an inwardly facing surface, and an outwardly facing surface;
- forming a central aperture having a bottom wall and a predetermined depth into the outwardly facing surface;
- radially slitting the inwardly facing surface of the gasket in the region of the aperture to a predetermined depth wherein the sum of the radial slit depth and the aperture depth is no less than the thickness of the gasket and where each of the depths of the slits and the aperture is less than the thickness of the gasket; and
- slitting the inwardly facing surface of the gasket to a predetermined depth in the region that is radially outward of the region defined by the aperture, whereby the slits in the region of the aperture define resilient flaps that normally close the aperture and the slits in the region radially outward of the aperture define a weakened region about the region defined by the aperture;
- wherein the sum of the aperture depth and the slit depth is greater than the thickness of the gasket.

* * * * *